(12) United States Patent
Sanghvi et al.

(10) Patent No.: US 6,822,089 B1
(45) Date of Patent: Nov. 23, 2004

(54) PREPARATION OF DEOXYNUCLEOSIDES

(75) Inventors: Yogesh S. Sanghvi, Encinitas, CA (US); Zhiqiang Guo, San Diego, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/537,843

(22) Filed: Mar. 29, 2000

(51) Int. Cl.$^7$ ............................................. C07H 19/00
(52) U.S. Cl. ................................ 536/27.11; 536/27.14; 536/28.2
(58) Field of Search .......................... 536/27.11, 27.14, 536/28.2

(56) References Cited

U.S. PATENT DOCUMENTS

| | | | | |
|---|---|---|---|---|
| 4,530,998 A | * | 7/1985 | Umezawa et al. ........ | 536/27.13 |
| 5,559,101 A | * | 9/1996 | Weis et al. ................. | 514/45 |
| 5,939,402 A | * | 8/1999 | Weis et al. ................. | 514/44 |
| 6,025,335 A | * | 2/2000 | Weis et al. ................. | 514/44 |
| 6,175,004 B1 | * | 1/2001 | Ross et al. ................. | 536/25.3 |
| 6,242,428 B1 | * | 6/2001 | Weis et al. ................. | 514/44 |
| 6,395,716 B1 | * | 5/2002 | Gosselin et al. ............ | 514/45 |

FOREIGN PATENT DOCUMENTS

| | | |
|---|---|---|
| EP | 0 999 218 A1 | 5/2000 |
| JP | 05-058990 A2 * | 3/1993 |
| JP | 08-301826 A2 * | 11/1996 |
| WO | WO 01/02608 A1 | 1/2001 |
| WO | WO01/34618 A2 * | 5/2001 |

OTHER PUBLICATIONS

Pankiewicz et al., "Nucleosides. 121. Improved and General Synthesis of 2'–Deoxy C–Nucleosides. Synthesis of 5–(2–Deoxy–β–D–erythro–pentofuranosyl)uracil, –1–methyluracil, –1,3–dimethyluracil, and –isocytosine," *Journal of Organic Chemistry*, 47(3), 485–488 (Jan. 29, 1982).*

Barton, D.H. et al., "Free Radical Deoxygenation of Thiocarbonyl Derivatives of Alcohols," in *Preparative Carbohydrate Chemistry*, Hanessian, S. (ed.), Marcel Dekker, Inc., New York, 1997, Chapter 8, 151–172.

Barton, D.H.R. et al.," The invention of radical reactions. Part XXIV.$^1$ relative rates of acylation and radical deoxygenation of secondary alcohols.$^+$, " *Tetrahedron Letters*, 1992, 48(36), 7435–7446.

Barton, D.H. et al., "Improved methods for the radical deoxygenation of secondary alcohols," *Tetrahedron Letters*, 1989, 30(20), 2619–2622.

Barton, D.H.R.; et al., "A new method for the deoxygenation of secondary alcohols," *J. Chem. Soc., Perkin Trans. I*, 1975, 1574–1585.

Bhat, B. et al., "Synthesis of Novel Nucleic Acid Mimics via the Stereoselective Intermolecular Radical Coupling of 3'–Iodo Nucleosides and Formaldoximines", *J. Org. Chem.*, 1996, 61, 8186–8199.

Dimock, S., et al., "An Efficient Multigram Synthesis of Monomers for the Preparation of Novel Oligonucleotides Containing Isosteric Non–Phosphorous Backbones," *Nucleosides & Nucleotides*, 1997, 16(7–9), 1629–1632.

Robins, M.J. et al., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides," *J. Am. Chem. Soc.*, 1983, 105, 4059–4065.

Robins, M.J. et al., "Smooth and efficient deoxygenation of secondary alcohols. A general procedure for the conversion of ribonucleosides to 2'–deoxynucleosides$^1$," *J. Am. Chem. Soc.*, 1981, 103, 932–933.

Copy of the EPO Supplementary European Search Report dated Jul. 25, 2003 (EP 01 91 8933).

Bertolini, R., et al., "Aromatic vs. Carbohydrate residues in the major groove: synthesis of 5–[(benzyloxy)methyl]pyrimidine nucleosides and their incorporation into oligonucleotides," XP–002248336, *Helvetica Chimica Acta*, 2000, 83, 1962–1976.

Dimock, S., et al., "An efficient multigram synthesis of monomers for the preparation of novel oligonucleotides containing isosteric non–phosphorous backbones," XP009008871, *Nucleosides & Nucleotides*, 1997, 16(7–9), 1629–1632.

Hammerschmidt, F., et al., "Eion einfacher weg zu D–Apio–β–D–furanosyl–und 2'–desoxyapio–β–D–furanosylnucleosiden," XP–002248334, *Liebigs Ann.*, 1995, 551–558 (English Abstract).

Papageorgiou, C., et al., "Synthesis of a protected 1–(2'–Deoxy–β–D–ribofuranosyl)–1*H*–benzimidazole 3'–Phosphate," XP 000647758, *Helvetica Chimica Acta*, 1987, 70, 138–141.

Varaprasad, C.V., et al., "Synthesis and structural studies of monocyclic 4'–Aza–L–Nucleosides," XP–002248335, *Tetrahedron*, 1999, 55, 13345–13368.

* cited by examiner

*Primary Examiner*—James O. Wilson
*Assistant Examiner*—Lawrence Crane
(74) *Attorney, Agent, or Firm*—Woodcock Washburn LLP

(57) ABSTRACT

Methods for preparing deoxynucleosides from their corresponding ribonucleosides by forming 3-tert-butylphenoxythiocarbonylderivatives of the ribonucleosides and subsequently effecting radical deoxygenation reactions at the carbon atoms to be deoxygenated.

18 Claims, 4 Drawing Sheets

PREPARATION OF DEOXYNUCLEOSIDES

FIELD OF THE INVENTION

The present invention is directed to methods for forming deoxynucleosides from their corresponding ribonucleosides by first forming tert-butylphenoxythiocarbonyl derivatives and subsequently effecting a radical deoxygenation reaction at the carbon attached to the site of the tert-butylphenoxythiocarbonyl group.

BACKGROUND OF THE INVENTION

The potential therapeutic use of oligonucleotides represents a new paradigm for novel drug discovery. Over the last decade, oligonucleotide based antisense, triplex, ribozyme and aptamer techniques have emerged as powerful tools in the discovery of more specific and effective drugs (Sanghvi, Y. S., *In Comprehensive Natural Product Chemistry*; Barton, D. H.; Nakanishi, K. (ed. in chief); vol. 7: DNA and Aspects of Molecular Biology; Kool. E. (ed.); Pergamon: New York, 1999, 285). Among these techniques, the antisense approach leads the trend with over a dozen oligonucleotides currently undergoing human clinical trials for the treatment of viral infections, cancers, and inflammatory disorders. For example, ISIS 2922 (formivirsen sodium) is a 21 mer antisense phosphorothioate that inhibits the replication of the human cytomegalovirun (HCMV). The recent success of antisense drugs in clinical trials is creating a growing demand for the manufacture of oligonucleotides.

Advances in automated synthesis on solid support and commercialization of synthetic nucleic acid building blocks now allows the generation and screening of an unprecedented number of synthetic oligonucleotides. Oligonucleotides are synthesized on automated DNA/RNA synthesizers with nucleoside phosphoramidites employed as the most commonly used monomers. Nucleoside phosphoramidites can be produced from the phosphitylation of 5'-dimethoxytrityl protected 2'-deoxynucleosides.

For the commercialization of antisense drugs, consumption of large amounts of 2'-deoxynucleosides are necessary. 2'-deoxynucleosides currently originate from natural sources, especially from salmon fish milt. The worldwide output of fish milt is about twenty thousand tons per year. From this, only about one hundred tons of DNA salt can be generated. The DNA salt is degraded to give approximately ten tons of 2'-deoxynucleosides in an even distribution of the four 2'-deoxynucleosides (dA, dC, dG, and T). A maximum of one ton of oligonucleotides can be produced from ten tons of 2'-deoxynucleosides, assuming that all ten tons would be available for oligonucleotide production.

According to our predictions, the market for the first three antisense drugs alone, not to mention the market for oligonucleotides used as other types of drugs and as diagnostic reagents, will require at least one ton of oligonucleotides, indicating that natural resources are insufficient to provide enough 2'-deoxynucleosides to meet future antisense drug demand. In addition, due to declining fish stock, fish milt may be an unreliable source of 2'-deoxynucleotides. Because the demand for 2'-deoxynucleosides exceeds the supply to such a great extent, a need exists for alternative sources of 2'-deoxynucleosides.

The supply of RNA and ribonucleosides is much greater than deoxynucleosides. RNA is derived from yeast and ribonucleosides can be produced in large amounts by fermentation processes. Due to their increased availability, ribonucleosides are much less expensive than 2'-deoxynucleosides. Methods exist for synthetically deriving deoxynucleosides from their ribonucleoside counterparts. Nevertheless, these methods are not economically feasible for the large scale production of 2'-deoxynucleosides. For example, ribonucleotides in their 5'-di or triphosphate form can be biosynthetically converted to their 2'-deoxy counterparts by ribonucleotide reductases. However, these processes are undesirable due to multiple inherent difficulties in the scaled-up production of 2'-deoxynucleosides catalyzed by these reductases.

Other possibilities exist for deriving deoxynucleosides from ribonucleosides. For instance, the chemical transformations used for converting alcohol groups to their corresponding deoxy derivatives are viable options. This chemistry involves radical chain reactions wherein thiocarbonyl derivatives of the alcohol groups are deoxygenated using free radical initiators and tributyltin hydride, as described by Barton and McCombie (Barton, D. H. R.; McCombie, S. J., *J. Chem. Soc., Perkin Trans. I*, 1975, 1574). These reactions are useful for the 2'-deoxygenation of ribonucleosides as well. (Robins, M. J.; Wilson, J. S., *J. Am. Chem. Soc.*, 1981, 103, 932, Robins, M. J.; Wilson, J. S.; Hansske, F., *J. Am. Chem. Soc.*, 1983, 105, 4059). Robins developed a thiocarbonyl reagent, phenyl chlorothionoformate (PhOCSCl, $44.75/5 g, Aldrich™ 1998–1999), that is introduced onto the 2'position of a ribonucleoside by a simple acylation. Chemical 2'-deoxygenation of the 2'-thiocarbonyl ribonucleoside is subsequently effected by a radical reaction. In addition to having a higher cost associated with the reagents these reactions use tin reagents for reductions which are toxic and difficult to dispose of.

The method developed by Robins was improved when the phenyl groups of the thiocarbonyl reagents were substituted with electron donating groups, such as halogens. (Barton, D. H.; Jaszberenyi, J. C., *Tetrahedron Letters*, 1989, 30, 2619, Barton, D. H. R.; Dorchak, J.; Jaszberenyi, J. C., *Tetrahedron Letters*, 1992, 36, 7435). Barton found that substituted phenyl chlorothionoformates, such as, 2,4,6-trichlorophenyl chlorothionoformate ($58.70/5 g Aldrich™ 1998–1999), or especially when pentafluorophenyl chlorothionoformate ($64.00/5 g Aldrich™ 1998–1999) is used to make the thiocarbonyl derivative, radical deoxygenation reaction rates with tributyltin hydride are considerably increased, occurring in minutes rather than hours. Additionally, the yields were found to be excellent. The electron withdrawing inductive effect of the substituents increases the radicophilicity of the thiocarbonyl group, thereby speeding up reaction rates. Although this method may be effective for the large scale production of 2'-deoxynucleosides from their corresponding ribonucleosides, the cost of the substituted phenylthiocarbonyl compounds is prohibitively high.

The use of a series of substituted 3'-phenyl thionocarbonates has been described wherein a free radical coupling using oximes mediated by bis(trimethylstannyl)-benzopinacolate. These reactions led to the formation of carbon-carbon bonds in the preparation of a series of dimeric nucleosides as mimics of nucleic acids (Bhat, B.; Swayze, E. E.; Wheeler, P.; Dimock, S.; Perbost, M.; Sanghvi, Y., *J. Org. Chem.*, 1996, 61, 8186, Dimock S.; Bhat, B.; Peoc'h, D.; Sanghvi, Y. S.; Swayze, E. E., *Nucleosides & Nucleotides*, 1997, 16(7–9) 1629).

The present invention addresses the need for cost-effective methods for the large-scale production of 2'-deoxynucleosides from their corresponding ribonucleosides.

SUMMARY OF THE INVENTION

The present invention provides processes for preparing a 2'-deoxynucleoside comprising the steps of:

selecting a ribonucleoside;

treating the ribonucleoside with at least one protecting agent for a time and under conditions effective to form a 3'-O,5'-O-bisprotected ribonucleoside;

contacting the 3'-O,5'-O-bisprotected ribonucleoside with an isomeric mixture of tert-butylphenyl chlorothionoformates, preferably comprising from about 87% to about 99% 3-tert-butylphenyl chlorothionoformate and from about 1% to about 13% 4-tert-butylphenyl chlorothionoformate, for a time and under conditions effective to form isomeric 2'-O-tert-butylphenoxythiocarbonyl derivatives of the bisprotected ribonucleoside; and treating the derivatives with a reducing agent for a time and under conditions effective to give the 2'-deoxynucleoside.

Preferred protecting agents include 1,3-dichloro-1,1,3,3-tetraisopropyldisiloxane.

A preferred reducing agent will convert the hydroxy to the hydrogen by a radical deoxygenation step.

According to one aspect of the present invention, a process for preparing a 2'-deoxynucleoside comprising the steps of:

selecting a ribonucleoside;

treating the ribonucleoside with at least one protecting agent for a time and under conditions effective to form a 3'-O,5'-O-bisprotected ribonucleoside;

contacting the 3'-O,5'-O-bisprotected ribonucleoside with an isomeric mixture of tert-butylphenyl chlorothionoformates, preferably comprising from about 87% to about 99% 3-tert-butylphenyl chlorothionoformate and from about 1% to about 13% 4-tert-butylphenyl chlorothionoformate, for a time and under conditions effective to form isomeric 2'-O-tert-butylphenoxythiocarbonyl derivatives of the bisprotected ribonucleoside; and treating the derivatives with a radical reagent and a radical initiator for a time and under conditions effective to form the 2'-deoxyribonucleoside.

In one aspect of the invention radical reagents include tributyltin hydride, solid supported tributyltin hydride, triethylsilyl hydride, a poly(alkyl)hydrosiloxane, or poly(methyl)hydrosiloxane.

In another aspect of the present invention a process for generating a 2'-deoxynucleoside radical is provided comprising the steps of:

selecting a ribonucleoside;

treating the ribonucleoside with at least one protecting agent for a time and under conditions effective to form the 3'-O,5'-O-bisprotected ribonucleoside;

contacting the 3'-O,5'-O-bisprotected ribonucleoside with an isomeric mixture of tert-butylphenyl chlorothionoformates, preferably comprising from about 87% to about 99% 3-tert-butylphenyl chlorothionoformate and from about 1% to about 13% 4-tert-butylphenyl chlorothionoformate, for a time and under conditions effective to form the isomeric 2'-O-tert-butylphenoxythiocarbonyl derivatives of the bisprotected ribonucleoside; and treating the derivatives with a radical reagent and a radical initiator for a time and under conditions effective to form the corresponding 2'-deoxynucleoside radical.

In a further aspect of the present invention, a process for making a 2',3'-dideoxynucleoside is provided comprising the steps of:

selecting a ribonucleoside;

treating the ribonucleoside with a first protecting agent for a time and under conditions effective to give a 5'-O-protected ribonucleoside;

treating the 5'-O-protected ribonucleoside with a second protecting agent for a time and under conditions effective to give a 2'-O,5'-O-protected ribonucleoside;

treating the 2'-O,5'-O-protected ribonucleoside with an acylating agent for a time and under conditions to give a 2'-O-protected-3'-O-acyl-5'-O-protected ribonucleoside;

treating the 2'-O-protected-3'-O-acyl-5'-O-protected ribonucleoside with a first deprotecting agent for a time and under conditions effective to give a 3'-O-acyl-5'-O-protected ribonucleoside;

contacting the 3'-O-acyl-5'-O-protected ribonucleoside with an isomeric mixture of tert-butylphenyl chlorothionoformates, preferably comprising from about 87% to about 99% 3-tert-butylphenyl chlorothionoformate and from about 1% to about 13% 4-tert-butylphenyl chlorothionoformate, for a time and under conditions effective to form isomeric 2'-O-tert-butylphenoxythiocarbonyl derivatives of the 3'-O-acyl-5'-O-protected ribonucleoside;

treating the derivatives with a radical reagent and a radical initiator for a time and under conditions effective to form a 3'-O-acyl-5'-O-protected-2'-deoxynucleoside radical;

subjecting the 3'-O-acyl-5'-O-protected-2'-deoxynucleoside radical to conditions effective to eliminate the 3'-O-acyl group thereby forming a 5'-O-protected-2',3'-didehydro-2',3'-dideoxynucleoside;

optionally treating the 5'-O-protected-2',3'-didehydro-2',3'-dideoxynucleoside with a second deprotecting agent for a time and under conditions effective give a 2',3'-didehydro-2',3'-dideoxynucleoside; and reducing the optionally deprotected 2',3'-didehydro-2',3'-dideoxynucleoside to give the 2',3'-dideoxynucleoside.

In a preferred embodiment the 5'-O-protecting group is acid-labile with trityl, monomethoxytrityl, dimethoxytrityl, trimethoxytrityl, 9-phenylxanthine-9-yl (Pixyl) or 9-(p-methoxyphenyl)xanthine-9-yl (MOX) being preferred.

Preferred conditions to effect elimination of the 3'-O-acyl group include at least one of exposure to light, heating and treatment with at least one chemical reagent.

A preferred 3'-O-acyl group has the formula:

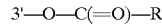

wherein R is substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl having 6 to about 14 carbon atoms, wherein the substituent groups are selected from alkyl, aryl, alkoxy, carboxy, benzyl, phenyl, halogen, alkenyl and alkynyl. A preferred R group is R is $C_1$–$C_{10}$ alkyl with $CH_3$ being more preferred.

In another aspect of the present invention, a process for preparing a 2',3'-dideoxynucleoside is provided comprising the steps of:

selecting a ribonucleoside;

treating the ribonucleoside with a protecting agent for a time and under conditions effective to give a 5'-O-protected ribonucleoside;

contacting the 5'-O-protected ribonucleoside with an isomeric mixture of tert-butylphenyl chlorothionoformates, preferably comprising from about 87% to about 99% 3-tert-butylphenyl chlorothionoformate and from about 1% to about 13% 4-tert-butylphenyl chlorothionoformate, for a time and under conditions effective to form isomeric 2',3'-O-bis-tert-butylphenoxythiocarbonyl derivatives of the 5'-O-protected ribonucleoside; and treating the derivatives with a radical reagent and a radical initiator for a time and under conditions effective to give the 2',3'-dideoxynucleoside.

In one aspect of the present invention a process for preparing a 5'-deoxynucleoside is provided comprising the steps of:

selecting a ribonucleoside;

treating the ribonucleoside with at least one protecting agent for a time and under conditions effective to form a 2'-O,3'-O-bisprotected ribonucleoside;

contacting the 2'-O,3'-O-bisprotected ribonucleoside with an isomeric mixture of tert-butylphenyl chlorothionoformates, preferably comprising from about 87% to about 99% 3-tert-butylphenyl chlorothionoformate and from about 1% to about 13% 4-tert-butylphenyl chlorothionoformate, for a time and under conditions effective to form isomeric 5'-O-tert-butylphenoxythiocarbonyl derivatives of the bisprotected ribonucleoside; and treating the derivatives with a radical reagent and a radical initiator for a time and under conditions effective to give the 5'-deoxynucleoside.

In a further embodiment transient protection of the 5'-hydroxyl position of the ribonucleoside is effected by treating the ribonucleoside with a labile protecting agent effective to protect the 5'-hydroxyl position prior to forming the 2'-O,3'-O-bisprotected ribonucleoside allowing selective removal of the 5'-protecting group by treatment with a deprotecting agent subsequent to formation of the 2'-O,3'-O-bisprotected ribonucleoside.

In a preferred embodiment the 5'-deoxynucleoside is formed by radical deoxygenation.

In yet another aspect of the present invention a process for preparing a 5'-deoxynucleoside comprising the steps of:

selecting a ribonucleoside;

treating the ribonucleoside with at least one protecting agent for a time and under conditions effective to form a 2'-O,3'-O-bisprotected ribonucleoside;

contacting the 2'-O,3'-O-bisprotected ribonucleoside with an isomeric mixture of tert-butylphenyl chlorothionoformates, preferably comprising from about 87% to about 99% 3-tert-butylphenyl chlorothionoformate and from about 1% to about 13% 4-tert-butylphenyl chlorothionoformate, for a time and under conditions effective to form isomeric 5'-O-tert-butylphenoxythiocarbonyl derivatives of the 2'-O,3'-O-bisprotected ribonucleoside; and treating the derivatives with a radical reagent and a radical initiator for a time and under conditions effective to form the corresponding 5'-deoxyribonucleoside.

In a preferred embodiment the radical reagent is tributyltin hydride, solid supported tributyltin hydride, triethylsilyl hydride, a poly(alkyl)hydrosiloxane or poly(methyl)hydrosiloxane.

In a further aspect of the present invention a process for converting a hydroxyl group to hydrogen comprising the steps of:

selecting a compound having the hydroxyl group;

contacting the compound with an isomeric mixture of tert-butylphenyl chlorothionoformates, preferably comprising from about 87% to about 99% 3-tert-butylphenyl chlorothionoformate and from about 1% to about 13% 4-tert-butylphenyl chlorothionoformate, for a time and under conditions effective to form a mixture of isomeric tert-butylphenoxythiocarbonyl derivatives of the compound; and treating the derivatives of the compound with a reducing agent for a time and under conditions effective to convert the hydroxyl group of the compound to hydrogen.

In preferred embodiments, the reducing step is effected by treating the derivatives with a radical initiator and a radical reagent to effectuate a radical deoxygenation reaction. Preferred radical initiators include azo initiators such as for example: AIBN (2,2'-azobisisobutyro-nitrile), ACN (VASO™; 1,1'-azobis[cyclohexanecarbo-nitrile]); diacyl peroxide initiators: benzoyl peroxide (dibenzoyl peroxide), and ultraviolet light; and polymerization initiators including for example VA-044, V-50, VA-061, V-501, VA-086, V-70, V-65B, V-601, V-59, and V-40. Preferred radical reagents include tributylin hydride, solid supported tributylin hydride, solid supported triethylsilyl hydride, and poly (alkyl)hydrosiloxane, such as poly(methyl)hydrosiloxane.

These and other features, aspects, and advantages of the present invention will become better understood with reference to the following description, appended claims and accompanying drawing.

DESCRIPTION OF PREFERRED EMBODIMENTS

Figure 1:
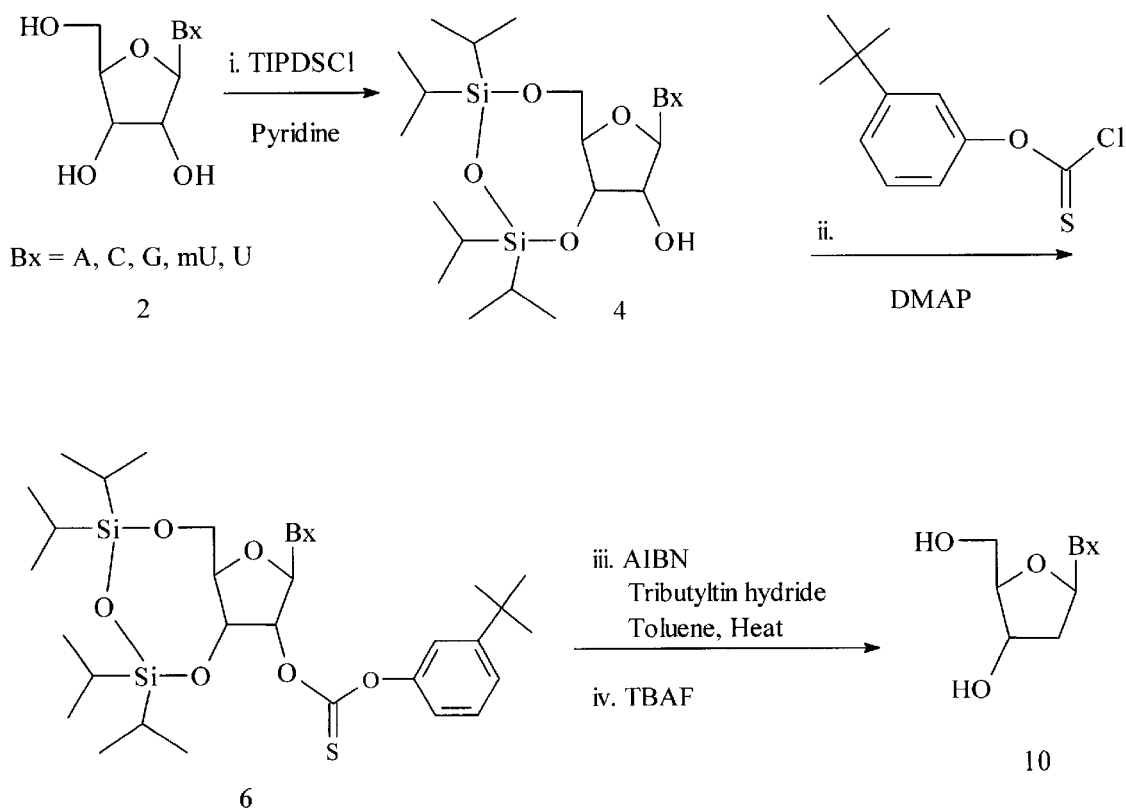
FIG. 1 shows the preparation of 2'-deoxynucleosides from their ribonucleosides.

The present invention is directed to methods for converting hydroxyl groups to hydrogen groups, more particularly, to deoxygenating ribonucleosides to form their corresponding deoxynucleosides by treating the ribonucleosides with an isomeric mixture of tert-butylphenyl chlorothionoformates to form the tert-butylphenyl thionocarbonyl derivatives followed by radical reactions which result in the desired deoxynucleosides. Preferably, the ribonucleosides are reacted with technical grade tert-butylphenyl chlorothionoformate which is available as an isomeric mixture of 3-tert-butylphenyl chlorothionoformate and 4-tert-butylphenyl chlorothionoformate to form the corresponding tert-butylphenoxythiocarbonyl derivatives. In preferred methods, the derivatives are subsequently reduced to their corresponding deoxyribonucleosides by a radical deoxygenation reaction whereby the derivatives are treated with a radical initiator to effect a radical reaction at the carbon atom bearing the hydroxyl group. In some preferred embodiments, the generated radical undergoes a hydrogen abstraction reaction, thereby replacing the hydroxyl group with a hydrogen group. In other preferred embodiments, the generated radical participates in an elimination reaction to form a 2',3' olefinic nucleoside which is subsequently reduced to the desired deoxynucleoside.

The use of technical grade 3-tert-butylphenyl chlorothionoformate in deoxygenation reactions is a significant advancement in the efficient and economic synthesis of the commercial (multi-kilogram) scale generation of 2'-deoxynucleosides from their ribonucleosides because it is much less expensive than the phenyl chlorothionoformates currently used for these purposes. Technical grade 3-tert-butylphenyl chlorothionoformate is commercially available as 93% 3-tert-butylphenyl chlorothionoformate with the remainder 4-tert-butylphenyl chlorothionoformate ($41.20/ 100 g, Aldrich™ 1998–1999) Surprisingly, technical grade tert-butylphenyl chlorothionoformate is a suitable reagent for the methods of the present invention despite the isomeric mixture of the intermediate thiocarbonyl ribonucleosides generated, and the electron donating inductive effect of the 3-tert-butyl group, which tends to make the thiocarbonyl derivatives less radicophilic. The reduced cost of the reagent compared to those known in the art allows for the efficient and economical production of multi-kilogram quantities of 2'-deoxynucleosides, 2',3'-didehydro-2',3'-dideoxynucleosides, 2',3'-dideoxynucleosides, 3'-deoxynucleosides and 5'-deoxynucleosides from their corresponding ribonucleosides.

Nucleosides

There are two principal series of nucleosides: the ribonucleosides, which contain D-ribose as the sugar component, and the deoxyribonucleosides, which generally contain 2-deoxy-D-ribose as the sugar component. Nucleosides can also be classified according to their heterocyclic bases or nucleobases, as being either a purine or a pyrimidine ribonucleoside or a purine or pyrimidine deoxyribonucleoside. Purine nucleosides, for example, include adenine (6-aminopurine), and guanine (2-amino-6-oxopurine). Pyrimidine nucleosides include, for example, uracil (2,4-dioxopyrimidine), thymine (5-methyl-2,4-dioxopyrimidine), and cytosine (4-amino-2-oxopyrimidine). Modified purine and pyrimidine nucleosides are well known in the art and included in the present invention. Some modifications include protecting groups for reactive functionalities. Any of a variety of protecting groups may be employed with the present invention. Examples of these protecting groups can be found in *Protective Groups in Organic Synthesis*, 3$^{rd}$ ed. T. W. Greene and P. G. M. Wuts, John Wiley & Sons, New York, N.Y., 1999, which is herein incorporated by reference in its entirety.

In addition to adenine, guanine, cytosine, uridine, and thymine, the present invention includes other synthetic and naturally occurring nucleobases that are well known in the art such as xanthine, hypoxanthine, 2-aminoadenine, 2-propyladenine, 6-methyladenine, 6-chloroadenine, 2-methylguanine, 7-methylguanine, 8-halo, amino, thiol, thioalkyl, hydroxyl and other 8-substituted adenines and guanines and other derivatives of adenine and guanine, 5-methylcytosine, 5-hydroxymethylcytosine, 5-halouracil and 5-halocytosine, 5-propynyluracil and 5-propynylcytosine, 6-azauracil, 6-azacytosine and 6-azathymine, 5-uracil (pseudouracil), 4-thiouracil, 5-trifluoromethyl and other 5-substituted uracils and cytosines. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch et al., *Angewandte Chemie, International Edition*, 1991, 30, 613.

Radical Chemistry

Radical chain chemistry is often employed for the transformation of a hydroxyl group of an alcohol to the corresponding deoxy derivative. As shown below, the alcohol 1, is first converted into a suitable thiocarbonyl derivative. These thiocarbonyl derivatives include the phenylthioxobenzoates 2, xanthates 3, thiocarbonylimidazolides 4 and phenylthiocarbonyl 5, groups (Barton, D. H.; Ferreira, J. A.; Jaszberenyi, J. C., *Preparative Carbohydrate Chemistry, Chapter 8, Free Radical Deoxygenation of Thiocarbonyl Derivatives of Alcohols*, Hanessian, S., Marcel Dekker, Inc., New York).

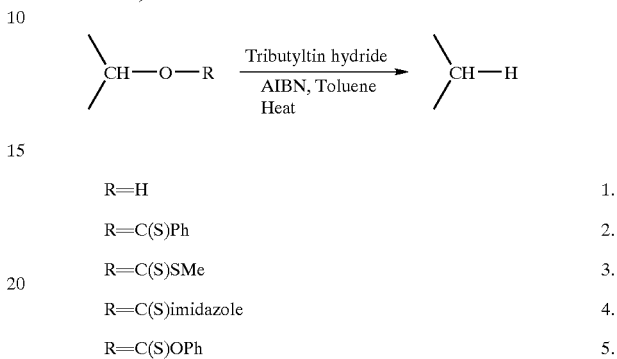

| | |
|---|---|
| R=H | 1. |
| R=C(S)Ph | 2. |
| R=C(S)SMe | 3. |
| R=C(S)imidazole | 4. |
| R=C(S)OPh | 5. |

Chemical deoxygenation can be accomplished by a radical reaction. Radical reactions normally involve initiation, propogation, and termination steps. The initiation step occurs when free radical initiators are heated, providing a source of radicals that sets off the desired radical chain reaction. Light may also initiate radical reactions. In the above example, the generated radicals react with the thiocarbonyl compound (2 through 5) generating intermediate thiocarbonyl carbon radical moieties. The intermediate radical moieties propagate a radical chain reaction. The carbon radical undergoes a hydrogen atom abstraction with a radical reagent (a hydride reagent, for example). This gives the desired deoxy derivative and generates the radical of the radical reagent (tributyl tin radical). Termination of the radical chain reaction occurs when the intermediate radical moiety or radical reagent (tributyl tin radical) is quenched by solvent or other hydrogen atom sources.

According to methods of the present invention, chemical deoxygenation of ribonucleosides by radical reactions provides a viable route to convert the readily available and inexpensive ribonucleosides into their corresponding 2'-deoxynucleosides. Radical initiators that are amenable to the present invention include azo initiators, AIBN (2,2'-azobisisobutyro-nitrile), ACN (VASO™; 1,1'-azobis[cyclohexanecarbo-nitrile]), and diacyl peroxide initiators, benzoyl peroxide (dibenzoyl peroxide), and ultraviolet light. There is a variety of polymerization initiators amenable to the present invention that are available from Wako Chemicals Inc., including for example VA-044™, V-50™, VA-061™, V-501™, VA-086™, V-70™, V-65B™, V-601™, V-59™, and V-40™.

Radical reagents are well known in the art and include tributyltin hydride (n-Bu$_3$SnH) which is a radical reagent used widely in reductive cleavage, radical dehalogenation, and intramolecular radical cyclizations; however, it is not without shortcomings. Tributylin hydride is highly toxic, the tin residues are difficult to separate from the desired products, and it is expensive. Separation techniques for isolating a desired organic compound from tin hydride reagents and byproducts have been developed, including chromatographic separations, solvent extractions and tin hydride fluorous reagents.

Alternatives to reagents such as tributyltin hydride include support bound tributyltin hydride reagent (Gerigk, U.; Gerlach, M.; Neumann, W. P.; Vieler, R.; Weintritt, V., *Synthesis*, 1990, 448); trialkyltin hydrides (trialkylsilanes), such as triethylsilyl hydride (triethylsilane), tris (trimethylsilyl)silane, tris(trimethylsilyl) silanethiol, heptamethyltrisilane-2-thiol; triaryltin hydrides (triarylstannanes), such as triphenylsilane, diphenylsilane, and phenylsilane; polymer supported tin hydride reagents, such as poly(alkyl)hydrosiloxane and poly(methyl) hydrosiloxane; dialkyl phosphites, such as dimethyl phosphite and diethyl phosphite; phosphorous containing moieties, such as hypophosphorous acid and its salts; N-ethylpiperidine hypophosphite, hypophosphorous acid and others (Barton, D. H.; Ferreira, J. A.; Jaszberenyi, J. C., *Preparative Carbohydrate Chemistry, Chapter 8, Free Radical* found that the use of technical grade 3-tert-butylphenyl chlorothionoformate allows for the clean conversion of 2'-deoxygenation of ribonucleosides without reaction rate problems or purification difficulties. Isomeric mixtures of 2'-O-(3-tert-butylphenoxythiocarbonyl)3',5'-O-TIDPS-ribonucleosides are sufficiently reactive and upon heating in the presence of a radical initiator, such as AIBN, and a radical reagent, such as tributyltin hydride, radical formation and subsequent hydrogen atom abstraction steps occur at the 2'position to give the desired 2'-deoxynucleosides. In some preferred embodiments, the deoxygenation of the isomeric mixture of 2'-O-(3-tert-butylphenoxythiocarbonyl) 3',5'-O-TIDPS-ribonucleosides is effected by heating the thiocarbonyl compound in the presence of ACN and triethylsilyl hydride. The 3', 5'-protecting groups can then be removed with suitable deprotecting agents that are well known in the art, for example, tetrabutylammonium fluoride (TBAF) in tetrahydrafuran (THF), to give the 2'-deoxynucleoside 10.

In some preferred embodiments, the ribonucleosides are regioselectively protected at other reactive functionalities of the nucleoside in addition to being protected at the 3'and 5'hydroxyl groups, prior to treatment with tert-butylphenyl chlorothionoformate. For example, amino groups can be protected with nitrogen protecting groups such as phthalimido, 9-fluorenylmethoxycarbonyl (FMOC), triphenylmethylsulfenyl, t-BOC or benzyl groups. Other amino protecting groups are well known in the art. Upon formation of the desired 2'-deoxynucleosides, these protecting groups are removed. Examples of such groups and methods for using them can be found in Agrawal et al., Protocols for Oligonucleotide Conjugates, Eds., Humana Press, New Jersey, 1994, Vol. 26, pp. 1–72, which is herein incorporated by reference in its entirety.

In one preferred embodiment of the present invention, the amino group of cytosine is protected by reacting the ribonucleoside with acetic anhydride in DMF under microwave treatment to acetylate the amino group before protection of the 3',5'-hydroxyl groups with TIDPS chloride (See, Nahar, P., *Tetrahedron Letters*, 1997, 38, 7253, herein incorporated by reference). Upon formation of the desired 2'-deoxynucleosides, the amino protecting group is removed with methanolic ammonia.

Figure 2:
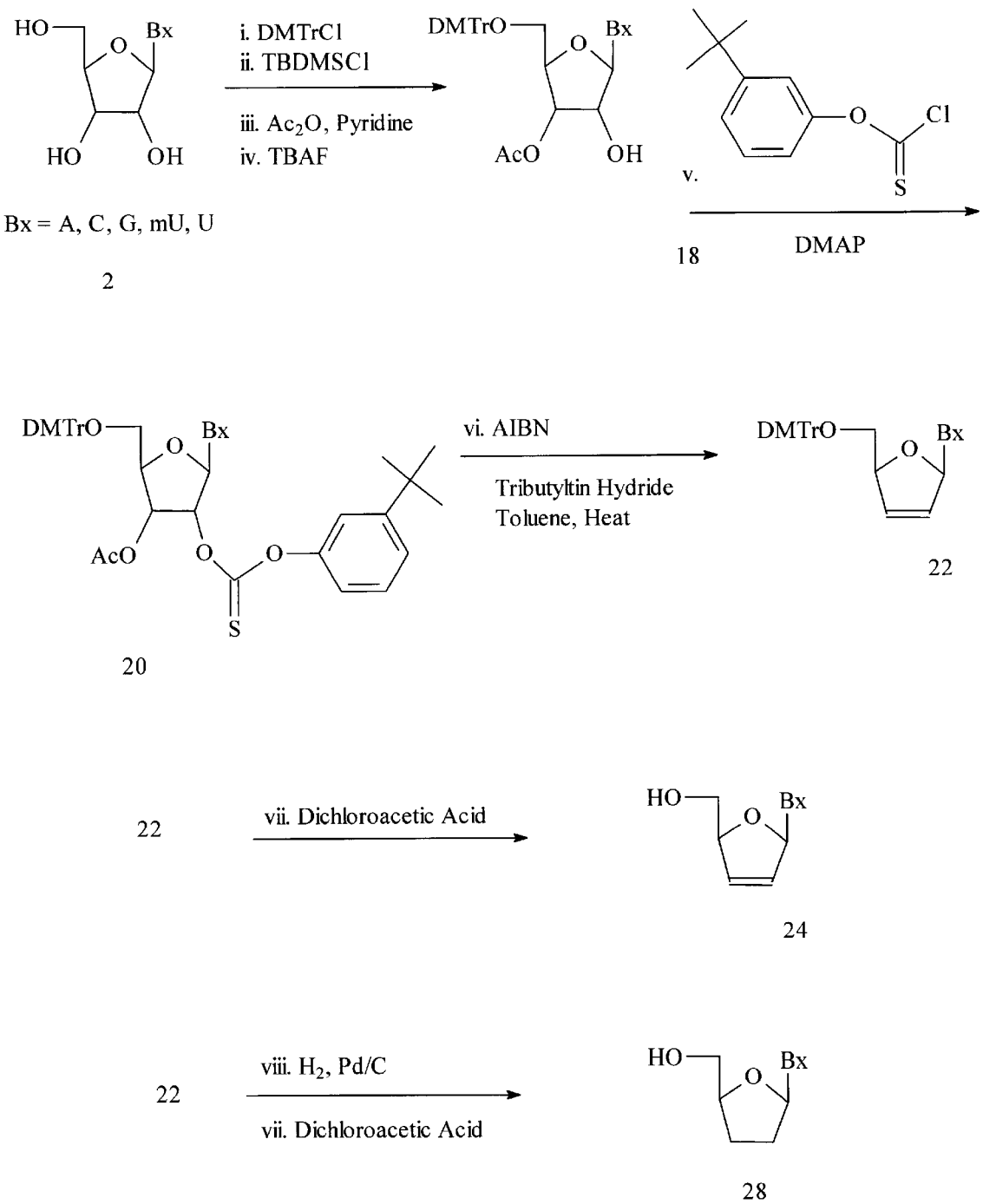
FIG. 2 shows the preparation of 2',3'-didehydro-2',3'-dideoxynucleosides and 2',3'-dideoxynucleosides from their ribonucleosides.

According to one embodiment of the present invention, referring to FIG. 2, for example, 2',3'-dideoxyribonucleosides are provided by selecting a ribonucleoside and protecting the 5'-hydroxyl group with a suitable protecting group. Preferably, the protecting group is an acid labile group, such as trityl, monomethoxytrityl, dimethoxytrityl (DMTr), trimethoxytrityl, 9-phenylxanthine-9-yl (Pixyl) or 9-(p-methoxyphenyl)xanthine-9-yl (MOX). Other well known hydroxyl protecting groups suitable for the present invention include those disclosed in *Protective Groups in Organic Synthesis*, 3$^{nd}$ ed. T. W. Greene and P. G. M. Wuts, John Wiley & Sons, New York, N.Y., 1999. The 5'-O-protected ribonucleoside is then protected at the 2'-hydroxyl position, preferably as the tert-butyldimethylsilyl (TBDMS) ether and further treated with a 3'-O protecting agent to form a 3'-O-acyl group, represented by the formula —C(O)—R, wherein R is substituted or unsubstituted $C_1$–$C_{10}$ alkyl, $C_2$–$C_{10}$ alkenyl, $C_2$–$C_{10}$ alkynyl, substituted or unsubstituted aryl having 6 to about 15 carbon atoms, wherein the substituent groups are selected from alkyl, alkenyl, alkynyl, aryl, alkoxy, carboxy, benzyl, phenyl, and halogen, with methyl being most preferred. The 2'-OTBDMS group is then removed with a suitable deprotection agent, such as TBAF, to give the 2'-hydroxyl, 3'-acetoxy, 5'-O-protected ribonucleoside. The protected ribonucleoside is then treated with technical grade 3-tert-butylphenyl chlorothionoformate to give the 2'-O-(3-tert-butylphenoxythiocarbonyl) derivative 20 as shown in FIG. 2, for example. Treatment of the thiocarbonyl derivative with a radical inititator and radical reagent gives the elimination product, 2',3'-didehydro-2',3'-dideoxy-5'-O-protected nucleoside 22. Treatment of the intermediate 22 with a suitable deprotecting agent, such as dichloroacetic acid, gives 2',3'-didehydro-2',3'-dideoxy nucleoside 24. Subsequent reduction of the double bond affords 2', 3'-dideoxynucleoside 28. Alternatively, the double bond may be reduced prior to deprotection of the 5'-O group. In preferred embodiments, reduction of the double bond is effected by a hydrogenation of the 2',3'double bond to give the saturated sugar ring system, 2',3'-dideoxynucleoside.

Reductive elimination of a trans or cis 2'-halo, 3'-O-acetate converts a ribonucleoside into its corresponding 2',3'-olefinic nucleoside. Chromous acetate, zinc/acetic acid and Zn/Cu couple have all been used to effect this transformation (Mansuri, M. M.; Starett, J. E., Wos, J. A.; Tortolani, D. R.; Brodfuehrer, P. R.; Howell, H. G.; Martin, J. C., *J. Org. Chem.*, 1989, 54, 4780, herein incorporated by reference). Similarly, generation of a 2'-deoxy radical in the presence of a 3'-O-acetate group in a ribonucleoside allows for a fast elimination reaction to occur to give the 2',3'-didehydro-2',3'-dideoxynucleoside.

Figure 3:
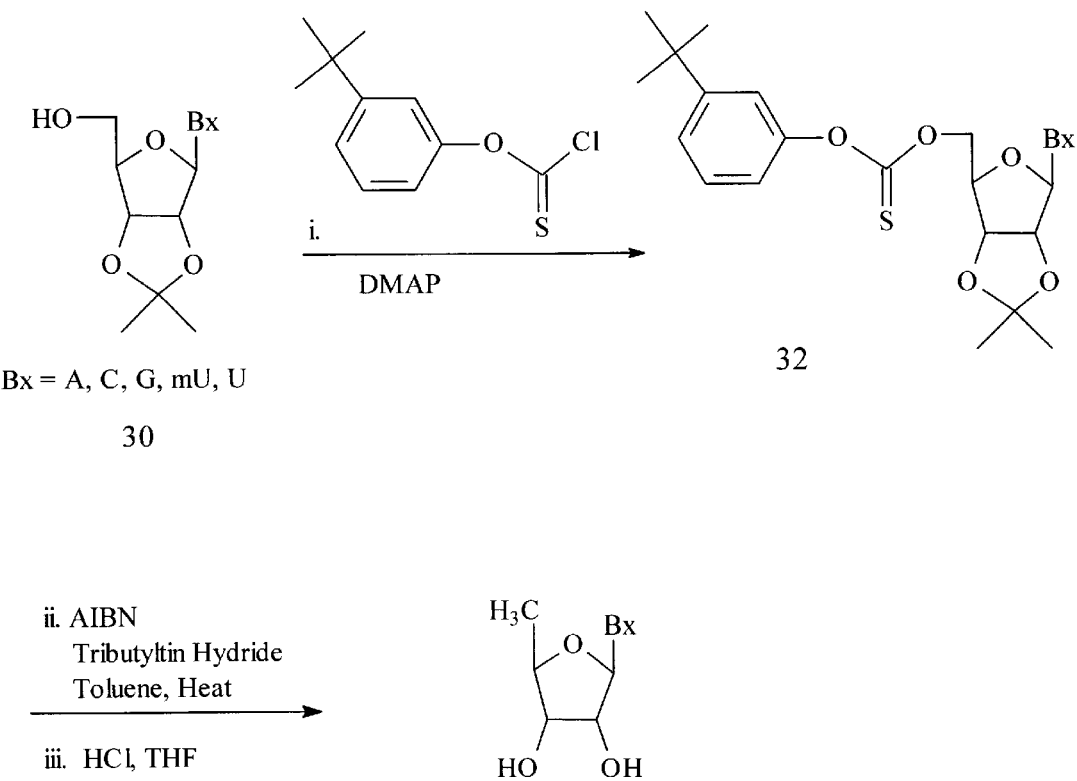
FIG. 3 shows the preparation of 5'deoxynucleosides from their ribonucleosides.

According to the present invention, radical deoxygenations of ribonucleosides with technical grade 3-tert-butylphenyl chlorothionoformate may also be effected to provide 5'-deoxynucleosides (4'-methylnucleosides). Referring to FIG. 3, for example, 5'-deoxynucleosides are prepared by providing a 2',3'-isopropylidenenucleoside 30 (available from Aldrich™ Milwaukee, Wis.) and treating it with technical grade 3-tert-butylphenyl chlorothionoformate to give a 2',3'-isopropylidene-5'-O-(3-tert-butyl phenoxythiocarbonyl) nucleoside 32. The 2',3'-isopropylidene-5'-O-(3-tert-butylphenoxythiocarbonyl) nucleoside is then treated with a radical initiator to generate a radical on the 4'-carbon atom. Hydrogen abstraction upon treatment with a suitable radical reagent provides the 2',3'-isopropylidene-4'-methyl-nucleoside 34. The 2',3'-isopropylidene-5'-deoxynucleoside is then treated with a suitable deprotection reagent, such as 1N HCl in THF to give the 5'-deoxynucleoside 36.

Figure 4:
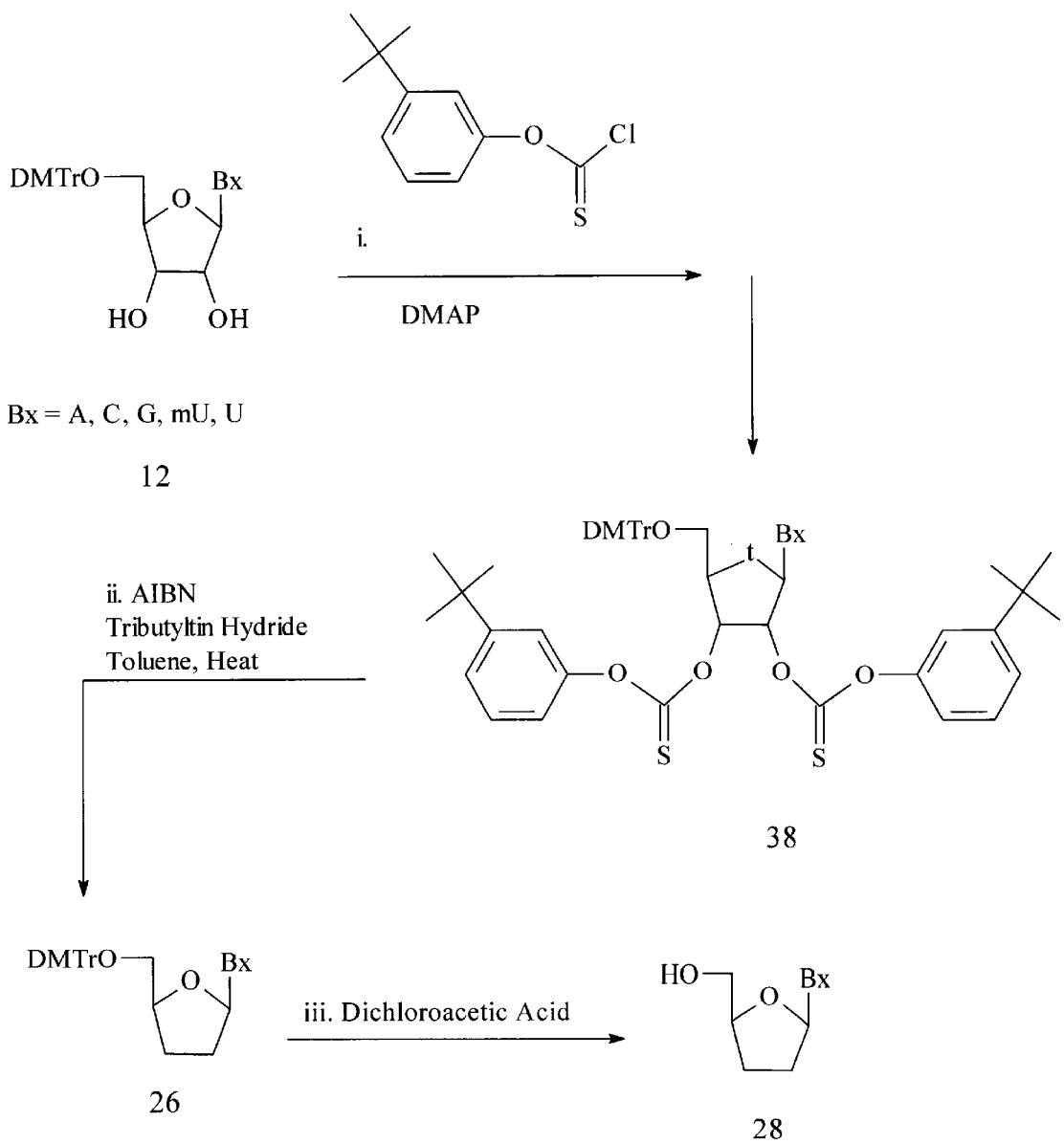
FIG. 4 shows the preparation of 2',3'-dideoxynucleosides from their ribonucleosides.

Other preferred embodiments of the present invention provide methods for using technical grade 3-tert-butylphenyl chlorothionoformate to deoxygenate the 3'-hydroxyl position of a ribonucleoside, as well as to effect the deoxygenation of any combination of several or all of the hydroxyl positions (2',3'or 5') of a ribonucleoside. Referring to FIG. 4, for example, a 5'-O-protected nucleoside is diacylated with technical grade 3-tert-butylphenyl chlorothionoformate to give 2'-O-(tert-butylphenoxythiocarbonyl)-3'-O-(tert-butylphenoxythio-carbonyl)-5'-O-protected nucleoside 38. The 2'-O-(3-tert-butylphenoxythio-carbonyl)-3'-O-(3-tert-butyl phenoxythiocarbonyl)-5'-O-protected nucleoside 38 is dideoxygenated with a radical initiator and a radical reagent to give the 5'-O-protected nucleoside 26. The 5'-O-protected is then treated with a suitable deprotecting agent to give the 2',3'-dideoxynucleoside 28.

Nucleosides of the present invention may have a substituent group covalently attached to the 2'-position of the sugar moiety or at various places on the nucleobase such as N2 or N6 position of purines and N4 or C5 position of pyrimidines. Preferably, substituents are attached at the 2' position of the sugar moiety.

A representative list of substituent groups amenable to the present invention includes hydrogen, hydroxyl, $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkynyl, O-alkylamino, O-alkylalkoxy, O-alkylaminoalkyl, O-alkyl imidazole, O-aryl, O-aralkyl, thiol, S-alkyl, S-alkenyl, S-alkynyl, S-aryl, S-aralkyl, amino, NH-alkyl, NH-alkenyl, NH-alkynyl, N-dialkyl, NH-aryl, NH-aralkyl, N-phthalimido, halogen (particularly fluoro), keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, heterocycle, carbocycle, polyamine, polyamide, polyalkylene glycol, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et. al. (*Critical Reviews in Therapeutic Drug Carrier Systems* 1992, 9, 249), each of which is herein incorporated by reference in its entirety. Further sugar modifications are disclosed in Cook, P. D., *Anti-Cancer Drug Design,* 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5 substitutions, hereby incorporated by reference in its entirety.

Additional sugar substituent groups amenable to the present invention include —SR and —NR$_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.,* 1997, 62, 3415–3420. 2'-NR$_2$ nucleosides are disclosed by Goettingen, M., *J. Org. Chem.,* 1996, 61, 6273–6281; and Polushin et al., *Tetrahedron Lett.,* 1996, 37, 3227–3230.

A preferred substituent includes 2'-methoxyethoxy [2'-O—CH$_2$CH$_2$OCH$_3$, also known as 2'-O-(2-methoxyethyl) or 2'-MOE] (Martin et al., *Helv. Chim. Acta,* 1995, 78, 486), i.e., an alkoxyalkoxy group. A further substituent is a 2'-dimethylaminooxyethoxy, i.e., a O(CH$_2$)$_2$ON(CH$_3$)$_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same", each of which is hereby incorporated by reference in its entirety. Other preferred modifications include 2'-methoxy (2-O—CH$_3$), 2'-aminopropoxy (2'-OCH$_2$CH$_2$CH$_2$NH$_2$) and 2'-fluoro (2'-F).

Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety Additional advantages and novel features of this invention will become apparent to those skilled in the art upon examination of the examples provided which should not be construed as limiting the appended claims.

EXAMPLES

General

All reagents and solvents are available from Aldrich™ (P.O. Box 355, Milwaukee, Wis., 53201) unless otherwise stated. Reactions are performed under an argon atmosphere unless otherwise noted. Column chromatography is carried out using normal phase silica gel. Eluent solvent ratios are given as volume/volume. Solvent gradients are carried out stepwise. Evaporations of solvents are performed in vacuo (50 torr) at 35° C. unless otherwise specified. NMR spectra are obtained with the following instruments: $^1$H NMR: Varian Gemini-200 (199.975 MHZ) or Varian Unity 400 (399.952 MHZ). $^{13}$C NMR: Varian Gemini-200 (50.289 MHZ). $^{31}$P NMR: Varian Gemini-200 (79.990 MHZ). NMR spectra are recorded using either deuteriochloroform, dimethylsulfoxide-d$_6$(DMSO) dimethylformamide-d$_7$, or deuteriomethanol as solvent (tetramethylsilane as internal standard). The following abbreviations are used to designate the multiplicity of individual signals: s=singlet, d=doublet, t=triplet, q=quartet, m=multiplet, dd=doublet of doublets, ddd=doublet of doublet of doublets, br s=broad singlet. Mass spectra are performed by Mass Consortium, San Diego, Calif.

Example 1

3',5'-O-TIDPS Adenosine

Procedure A

To a solution of adenosine (2A) (1.335 g, 5.00 mmol) in DMF (25 mL) and pyridine (18 mL), cooled to 0° C., is added 1,3-dichloro-1,1,3,3-tetraisopropyldisiloxane (TIDPS chloride, Markiewicz reagent) (1.58 g, 5.00 mmol). The mixture is stirred at 0° C. for 30 minutes followed by stirring at room temperature for 5 hours. The solution is concentrated in vacuo and the residue is co-evaporated with toluene (2×10 mL). The residue is partitioned between ethyl acetate (100 mL) and cold 1 N HCl/water (100 mL). The layers are separated and the organic layer is washed with saturated NaHCO$_3$ (50 mL), water (50 mL), brine (50 mL), and dried over anhydrous sodium sulfate. Filtration and evaporation of the solvents gives the protected 3',5'-O-TIDPS adenosine.

Example 2

2'-O-(3-tert-butylphenoxythiocarbonyl)-3',5'-O-TIDPS Adenosine

Procedure B

To a solution of 3',5'-O-TIDPS adenosine (4A) (1.335 g, 5.00 mmol) in acetonitrile (40 mL), cooled to −20 0° C., is added 4-(dimethylamino)pyridine (DMAP) (1.25 g, 10.20 mmol) and 3-tert-butylphenyl chlorothionoformate (1.26 g, 5.50 mmol, 93%, remainder 4-tert-butylphenyl chlorothiono-formate). The solution is warmed to room temperature and is stirred for 16 hours. The solution is concentrated in vacuo and the residue is partitioned between ethyl acetate (100 mL) and cold 1 N HCl/water (100 mL).

The layers are separated and the organic extract is washed with saturated $NaHCO_3$ (50 mL), water (50 mL), brine (50 mL), and is dried over $Na_2SO_4$. Filtration, evaporation of the solvents, and purification by silica gel column chromatography (5% methanol/dichloromethane) gives the 2'-O-(3-tert-butylphenoxythiocarbonyl)-3',5'-O-TIDPS adenosine as a white powder (3.06 g, 98.7% for two steps). Melting point 143–145° C. MS (FAB) m/z 702.3198, ($MH^+$ [$C_{33}H_{52}N_5O_6SSi_2$]=702.3177).

Example 3

2'-Deoxy-3',5'-O-TIPDS-Adenosine

Procedure C

To a solution of 2'-O-(3-tert-butylphenoxy-thiocarbonyl)-3',5'-O-TIDPS adenosine (3.06 g, 4.36 mmol) in toluene (50 mL) is added AIBN (0.14 g, 0.87 mmol) and tributyltin hydride (2.35 mL, 8.73 mmol). The solution is deoxygenated with argon for 20 minutes and heated to 100° C. for 4 hours. Another batch of AIBN (0.14 g, 0.87 mmol) is added after 2 hours. The solution is concentrated in vacuo and the residue is purified by silica gel column chromatography (5% methanol/dichloromethane) to give 2'-deoxy-3',5'-O-TIPDS-adenosine (1.764 g, 82.0%). MS (FAB) m/z 494 ($MH^+$[$C_{22}H_{40}N_5O_4Si_2$]=494).

Example 4

2'-Deoxyadenosine

Procedure D

To a solution of 2'-deoxy-3',5'-O-TIPDS-adenosine, (8A) (2.557 g, 5.18 mmol) in THF (15 mL) is added TBAF (10.4 mL, 1M in THF). The solution is stirred at room temperature for 5 hours. The solution is concentrated in vacuo and the residue is partitioned between water (100 mL) and dichloromethane (100 mL). The layers are separated and the aqueous layer is washed with dichloromethane (2×50 mL). The aqueous phase is concentrated in vacuo, and the residue is purified on a column of Dowex 1-X2 ($OH^-$) resin. The product is eluted with water, collected, evaporated and crystallized in ethanol to give 2'-deoxyadenosine (10A) (1.187 g, 91.2%). Melting point 190–19°2 C. $^1$H NMR (DMSO) d 2.27 (ddd, J=13.2, 6.1, 2.8 Hz, 1, $H_{2'}$), 2.75 (ddd, J=13.2, 7.8, 5.8 Hz, 1, $H_{2''}$), 3.60 (m,2, $H_{5',5''}$), 3.90 (dd, J=6.6, 4.0 Hz, 1, $H_{3'}$), 4.43 (m, 1, $H_{4'}$), 5.27 (t, J=5.9 Hz, 1, $OH_5$), 5.34 (d, J=3.9 Hz, 1, $OH_3$), 6.37 (dd, J=6.1, 7.8 Hz, 1, $H_{1'}$), 7.35 (br s, 2, $NH_2$), 8.15 & 8.36 (s, s, 2, $H_{2,8}$). MS (FAB) m/z 252.1090 ($MH^+$[$C_{10}H_{14}N_5O_3$]=252.1097.

Example 5

4-N-Acetylcytidine

To a solution of cytidine (1.22 g, 5.00 mmol) in DMF(40 mL) is added acetic anhydride (0.94 mL, 10.00 mmol). The solution is treated with microwave radiation (Panasonic, 1000 Watts) at full power for 40 seconds. The solution is concentrated in vacuo and the residue is co-evaporated with methanol (2×20 mL) to give 4-N-acetyl-cytidine (1.43 g, 95.0%) as a white powder. MS (FAB):m/z 286 ($MH^+$).

Example 6

3',5'-O-TIDPS-4-N-Acetylcytidine

4-N-acetylcytidine (1.425 g, 5.00 mmol) is treated with TIDPS chloride (1.58 g, 5.00 mmol) as per Procedure A to give 3',5'-O-TIDPS-4-N-acetylcytidine (2.407 g, 91.3%). MS (FAB) m/z 550.2380 ($MNa^+$[$C_{23}H_{41}N_3O_7NaSi_2$]=550.2381).

Example 7

2'-O-(3-tert-Butylphenoxythiocarbonyl)-3',5'-O-TIDPS-4-N-Acetylcytidine

3',5'-O-TIDPS-4-N-acetylcytidine (2.407 g, 4.57 mmol) is treated with DMAP (4.50 g, 36.80 mmol) and 3-tert-butylphenyl chlorothionoformate (1.15 g, 5.00 mmol) as per Procedure B to give 2'-O-(3-tert-butylphenoxy-thiocarbonyl)-3',5'-O-TIDPS-4-N-acetylcytidine. MS (FAB) m/z 742.3001 ($MNa^+$[$C_{34}H_{53}N_3O_8NaSSi_2$]=742.2990).

Example 8

2'-Deoxy-3',5'-O-TIDPS-4-N-Acetylcytidine

2'-O-(3-tert-Butylphenoxythiocarbonyl)-3',5'-O-TIDPS-4-N-acetylcytidine is treated with AIBN (0.19 g, 1.15 mmol) and tributyltin hydride (3.34 g, 11.50 mmol) as per Procedure C to give 4-N-acetyl-2'-deoxy-3',5'-O-TIPDS-cytidine (2.18 g, 93.0%). MS (FAB) m/z 512.2633 ($MH^-$ [$C_{23}H_{42}N_3O_6Si_2$]=512.2612).

Example 9

2'-Deoxy-4-N-Acetylcytidine

To a solution of 4-N-acetyl-2'-deoxy-3',5'-O-TIPDS-cytidine (2.40 g, 4.70 mmol) in THF (20 mL) is added (TBAF) (9.4 mL, 1M in THF). The solution is stirred at room temperature for 16 hours. The solution is concentrated in vacuo to give 2'-deoxy-4-N-acetylcytidine.

Example 10

2'-Deoxycytidine

2'-deoxy-4-N-acetylcytidine is treated with methanolic ammonia overnight. The solution is concentrated in vacuo, and the residue is dissolved in water (100 mL) and is washed with dichloromethane (2×50 mL). The aqueous phase is evaporated in vacuo and the residue is purified on a column of Dowex 1-X2 ($OH^-$)resin. The product is eluted with water, and the fractions are collected, evaporated and the residue is crystallized in methanol to give 2'-deoxycytidine (0.902 g, 84.6%). Melting point 208–210° C. $^1$H NMR (DMSO) d 1.94(dt, J=13.2, 6.1 Hz, 1, $H_{2'}$), 2.12 (ddd, J=13.2, 6.0, 3.3 Hz, 1, $H_{2''}$),3.07 (m, 2, $H_{5',5''}$), 3.77 (dd, J=6.9, 3.8 Hz, 1, $H_{3'}$), 4.21 (dd, J=5.9, 3.2 Hz, 1, $H_{4'}$), 5.02 (t, J=5.0 Hz, 1, $OH_{5'}$), 5.23 (d, J=4.1 Hz, 1, $OH_{3'}$), 5.75 (d, J=7.4 Hz, 1, $H_5$), 6.17 (t, J=6.7 Hz, 1, $H_{1'}$), 7.21 (br s, 2, $NH_2$), 7.81 (d, J=7.4 Hz, 1, $H_6$) ppm. MS (FAB) m/z 228.0990 ($MH^+$[$C_9H_{14}N_3O_4$]=228.0984).

Example 11

3',5'-O-TIDPS Guanosine

To a solution of guanosine (1.133 g, 4.00 mmol) in pyridine (4 mL) and DMF (60 mL) is added TIDPS chloride (1.26 g, 4.00 mmol). The solution is stirred at room temperature for 5 hours. The solution is slowly added to 1 L of vigorously stirred ice-water. The resulting precipitate is collected by filtration and washed thoroughly with water. Recrystallization of the crude solids from ethanol gives 3',5'-O-TIDPS guanosine (1.76 g, 83.8%). MS (FAB) m/z 548.2345 ($MNa^+$[$C_{22}H_{39}N_5O_6NaSi_2$]=548.2337).

Example 12

2'-O-(3-tert-Butylphenoxythiocarbonyl)-3',5'-O-TIDPS Guanosine

3',5'-O-TIDPS guanosine (1.76 g, 3.35 mmol) is treated with DMAP (0.84 g, 6.88 mmol) and 3-tert-butylphenyl chlorothionoformate (0.842 g, 3.68 mmol) as per Procedure B to give 2'-O-(3-tert-butylphenoxythiocarbonyl)-3',5'-O-TIDPS guanosine (6G) a white powder (1.83 g, 76.0%). MS (FAB) m/z 740.2955 (MNa$^+$[C$_{33}$H$_{51}$N$_5$O$_7$NaSSi$_2$]= 740.2945).

Example 13

2'-Deoxy-3',5'-O-TIDPS Guanosine

2'-O-(3-tert-Butylphenoxythiocarbonyl)-3',5'-O-TIDPS guanosine (6G) (1.83 g, 2.54 mmol) is treated with AIBN (83 mg, 0.51 mmol) and tributyltin hydride (1.48 g, 1.37 mL, 5.09 mmol) as per Procedure C to give 2'-deoxy-3',5'-O-TIDPS guanosine.

Example 14

2'-Deoxyguanosine

2'-Deoxy-3',5'-O-TIDPS guanosine is treated with TBAF (5.1 mL, 1M in THF) as per Procedure D. The residue is purified on a column of Dowex 1-X2 (OH$^-$) resin. The product is eluted with 0.25 M Et$_4$N$^+$HCO$_3^-$(TEAB) buffer in water. The fractions are collected and concentrated in vacuo. The residue is co-evaporated with water (4×10 mL), and crystallized in water to give 2'-deoxyguanosine (10G) (0.506 g, 80.0% for two steps). Melting point>300° C. (decomposes). $^1$H NMR (DMSO) d 2.20 (ddd, J=13.1, 6.1, 2.8 Hz, 1, H$_{2'}$), 2.52 (m, 1, H$_{2''}$), 3.55 (m, 2, H$_{5',5''}$), 3.82 (dd, J=7.0, 4.4 Hz, 1, H$_{3'}$), 4.35 (m, 1, H$_{4'}$), 4.97 (t, J=5.5 Hz, 1, OH$_5$), 5.28 (d, J=3.9 Hz, 1, OH$_3$), 6.14 (dd, J=7.7, 6.1 Hz, 1, H$_{1'}$), 6.47 (br s, 2, NH$_2$), 7.94 (s, 1, H$_8$), 10.64 (s, 1, NH$_1$) ppm. MS (FAB) m/z 268.1056 (MH$^+$[C$_{22}$H$_{41}$N$_5$O$_4$]= 268.1046).

Example 15

3',5'-O-TIDPS 5-Methyluridine 5-methyluridine (1.925 g, 7.46 mmol) is treated with TIDPS chloride (2.36 g, 2.40 mL, 0.75 mmol) as per Procedure A to give 3',5'-O-TIDPS 5-methyluridine (4 mU) (3.73 g, 99.5%). MS (FAB) m/z 501.2450 (MH$^+$ [C$_{22}$H$_{41}$N$_2$O$_7$Si$_2$]=501.2441).

Example 16

2'-O-(3-tert-Butylphenoxythiocarbonyl)-3',5'-O-TIDPS 5-Methyluridine

3',5'-O-TIDPS 5-methyluridine (4 mU)(3.73 g, 7.45 mmol) is treated with DMAP (1.87 g, 2.05 mmol) and 3-tert-butylphenyl chlorothionoformate (1.88 g, 8.20 mmol) as per Procedure B to give 2'-O-(3-tert-butylphenoxythiocarbonyl)-3',5'-O-TIDPS 5-methyluridine (4.87 g, 94.4%). MS(FAB) m/z 715.2877 (MNa$^+$[C$_{33}$H$_{52}$N$_2$O$_8$NaSSi$_2$]= 715.2867).

Example 17

3',5'-O-TIPDS-Thymidine

2'-O-(3-tert-Butylphenoxythiocarbonyl)-3',5'-O-TIDPS 5-methyluridine (4.87g, 7.03 mmol) is treated with AIBN (0.34 g, 1.41 mmol) and tributyltin hydride (4.73 mL, 17.60 mmol) as per Procedure C to give 3',5'-O-TIPDS-thymidine (3.29 g, 96.6%). MS (FAB) m/z 485.2491 (MH$^+$ [C$_{22}$H$_{41}$N$_2$O$_6$Si$_2$]=485.2503).

Example 18

Thymidine

3',5'-O-TIPDS-thymidine (3.29 g, 6.79 mmol) is treated with TBAF (1M in THF) as per Prodedure D. The residue is purified by silica gel column chromatography (10% methanol/dichloromethane). The fractions are collected and concentrated in vacuo to give a residue. The residue is crystallized in methanol to give thymidine (1.468 g, 89.2%). Melting point 187–189° C. $^1$H NMR (DMSO) d 1.78 (s, 3, CH$_3$), 2.10 (m, 2, H$_{2',2''}$), 3.59 (dd, J=8.5, 3.6 Hz, 2, H$_{5',5''}$), 3.77 (dd, J=4.3, 1.0 Hz, 1, H$_3$), 4.25 (m, 1, H$_{4'}$), 5.03 (t, J=5.1 Hz, 1, OH$_5$), 5.24 (d, J=4.3 Hz, 1, OH$_3$), 6.18 (t, J=6.9 Hz, 1, H$_{1'}$), 7.71 (s, 1, H$_6$), 11.29 (br s, 1, NH$_3$) ppm. MS (FAB) m/z 242.0910 (MH$^+$[C$_{10}$H$_{14}$N$_2$O$_5$]=242.0903).

Example 19

3',5'-O-TIDPS Uridine

Uridine (2U) (0.972 g, 4.00 mmol) is treated with TIPDS chloride (1.26 g, 4.00 mmol) as per Procedure A to give 3',5'-O-TIDPS uridine (1.71 g 88.1%).

Example 20

2'-O-(3-tert-Butylphenoxythiocarbonyl)-3',5'-O-TIDPS Uridine

3',5'-O-TIDPS uridine (1.71 g, 3.52 mmol) is treated with DMAP (0.881 g, 7.21 mmol) and 3-tert-butyl phenyl chlorothionoformate (0.887 g, 3.87 mmol) as per Procedure B to give 2'-O-(3-tert-Butylphenoxythiocarbonyl)-3',5'-O-TIDPS Uridine (2.40 g, 100%). MS (FAB) m/z 679.2895 (MH$^+$ [C$_{32}$H$_{51}$N$_2$O$_8$SSi$_2$]=679.2905).

Example 21

2'-Deoxy-3',5'-O-TIPDS-Uridine

2'-O-(3-tert-Butylphenoxythiocarbonyl)-3',5'-O-TIDPS uridine (2.40 g, 3.54 mmol) is treated with AIBN (0.12 g, 0.71 mmol) and tributyltin hydride (1.43 mL, 5.32 mmol) as per Procedure C to give 2'-deoxy-3',5'-O-TIPDS-uridine (8U). MS (FAB) m/z 493.2180 (M Na$^+$ [C$_{21}$H$_{38}$N$_2$O$_6$NaSi$_2$]=493.2166).

Example 22

2'-Deoxyuridine

2'-Deoxy-3',5'-O-TIPDS-uridine is treated with TBAF (7.4 mL, 1M in THF) as per Procedure D. The residue is purified by silica gel column chromatography (10% methanol/dichloromethane). The fractions are combined, concentrated in vacuo and the residue is recrystallized from ethanol to give 2'-deoxyuridine (0.599 g, 74.3% over two steps). Melting point 162–163° C., $^1$H NMR (DMSO) d 2.08 (m, 2, H$_{2',2''}$), 3.56 (m, 2, H$_{5',5''}$), 3.79 (m, 1, H$_3$), 4.23 (m, 1, H$_{4'}$), 5.02 (t, J=5.1 Hz, 1, OH$_5$), 5.26 (d, J=4.1 Hz, OH$_3$), 5.56 (d, J=8.2 Hz, 1, H$_5$), 6.17 (t, J=6.8 Hz, 1, H$_{1'}$), 7.86 (d, J=8.2 Hz, 1, H$_6$), 11.31 (br s, 1, NH$_3$). MS (FAB) m/z 229.0822 (MH$^-$[C$_9$H$_{13}$N$_2$O$_5$]=229.0824).

Example 23

Preparation of 5'-O-DMTr-Adenosine, 2'-OTBDMS-5'-O-DMTr-Adenosine (14A), 2'-O-TBDMS-3'-O-Acetoxy-5'-O-DMTr-Adenosine (16A), and 3'-O-Acetoxy-5'-O-DMTr-Adenosine Adenosine is treated with 4,4'-dimethoxytriphenylmethyl chloride (DMTrCl) and DMAP in DMF to give 5'-O-DMTr-adenosine. 5'-O-DMTr-adenosine is treated with tert-butyldimethylsilyl chloride, silver nitrate and pyridine in THF to give 2'-OTBDMS-5'-O-DMTr-adenosine. 2'-OTBDMS-5'-O-DMTr-adenosine is treated with acetic anhydride in pyridine or DMAP to give 2'-O-TBDMS-3'-O-acetoxy-5'-O-DMTr-adenosine. 2'-O-TBDMS-3'-O-acetoxy-5'-O-DMTr-adenosine is treated with TBAF to give 3'-acetoxy-5'-O-DMTr-adenosine.

Example 24

Preparation of 2'-O-(3-tert-butylphenoxythiocarbonyl)-3'-O-Acetoxy-5'-O-DMTr-Adenosine 3'-Acetoxy-5'-O-DMTr-adenosine is treated with DMAP and 3-tert-butylphenyl chlorothionoformate as per Procedure B to give 2'-O-(3-tert-butylphenoxythiocarbonyl)-3'-O-acetoxy-5'-O-DMTr-adenosine Example 25

Preparation of 2',3'-Didehydro-2',3'-Dideoxy-5'-O-DMTr-Adenosine

2'-O-(3-tert-butylphenoxythiocarbonyl)-3'-O-acetoxy-5'-O-DMTr-adenosine (20A) is treated with AIBN and tributyltin hydride as per Procedure C to give 2',3'-didehydro-2',3'-dideoxy-5'-O-DMTr-adenosine Example 26

Preparation of 2',3'-Didehydro-2',3'-dideoxyadenosine

2',3'-Didehydro-2',3'-dideoxy-5'-O-DMTr-adenosine is deprotected by treatment with dichloroacetic acid to give title compound.

Example 27

Preparation of 2',3'-Dideoxy-Adenosine

2',3'-Didehydro-2',3'-dideoxy-5'-O-DMTr-adenosine is treated with 5–10% palladium on carbon in a hydrogen atmosphere to give 2',3'-dideoxy-5'-O-DMTr-adenosine which is further treated with dichloroacetic acid to give the title compound.

Example 28

Preparation of 3'-Isopropylidene-5'-O-(3-tert-butyl phenoxythiocarbonyl)Adenosine 2',3'-isopropylideneadenosine is treated with technical grade 3-tert-butylphenyl chlorothionoformate as per Procedure B to give 2',3'-isopropylidene-5'-O-(3-tert-butyl phenoxythiocarbonyl) adenosine Example 29

Preparation of 2',3'-Isopropylidene-4'-Methyl-Adenosine and 4'-Methyl-Adensosine 2',3'-Isopropylidene-5'-O-(3-tert-butyl phenoxythiocarbonyl) adenosine is deoxygenated with AIBN and tributyltin hydride as per Procedure C to give 2',3'-isopropylidene-4-methyl-adenosine. 2',3'-isopropylidene-4-methyl-adenosine is treated with 1N HCl in THF (1:1) at room temperature to give 5'-methyl-adensosine Example 30

Preparation of 2'-O-(3-tert-butyl phenoxythiocarbonyl)-3'-O-(3-tert-Butyl Phenoxythiocarbonyl)-5'-O-DMTr Adenosine 5'-O-DMTr-Adenosine is treated with DMAP and 3-tert-butylphenyl chlorothionoformate as per Procedure B to give 2'-O-(3-tert-butylphenoxythiocarbonyl)-3'-O-(3-tert-butylphenoxythiocarbonyl)-5'-O-DMTr-adenosine.

Example 31

Preparation of 5'-O-DMTr-2',3'-Dideoxyadenosine and 2',3'-Dideoxyadenosine

2'-O-(3-tert-Butylphenoxythiocarbonyl)-3'-O-(3-tert-butylphenoxythiocarbonyl)-5'-O-DMTr-adenosine is treated with AIBN and tributyltin hydride as per Procedure C to give 2',3'-dideoxy-5'-O-DMTr-adenosine. 2',3'-Dideoxy-5'-O-DMTr-adenosine is treated with dichloroacetic acid to give 2',3'-dideoxyadenosine.

Those skilled in the art will appreciate that numerous changes and modifications may be made to the preferred embodiments of the present invention, and that such changes and modifications may be made without departing from the spirit of the invention. It is, therefore, intended that the spirit and scope of the appended claims should not be limited to the description of the preferred embodiments contained herein, but, that the appended claims cover all such equivalent variations as fall within the true spirit and scope of the invention.

What is claimed is:

1. A process for preparing a 2'-deoxynucleoside comprising the steps of:
   selecting a ribonucleoside;
   treating said ribonucleoside with at least one protecting agent for a time and under conditions effective to form a 3'-O,5'-O-bisprotected ribonucleoside;
   contacting said 3'-O,5'-O-bisprotected ribonucleoside with an isomeric mixture of tert-butylphenyl chlorothionoformates for a time and under conditions effective to form isomeric 2'-O-tert-butylphenoxythiocarbonyl derivatives of said bisprotected ribonucleoside; and
   treating said derivatives with a triethylsilyl hydride or poly(alkyl)hydrosiloxane radical reagent and a radical initiator for a time and under conditions effective to form said 2'-deoxyribonucleoside.

2. The process of claim 1 wherein said mixture comprises 3-tert-butylphenyl chlorothionoformate and 4-tert-butylphenyl chlorothionoformate.

3. The process of claim 2 wherein said mixture comprises from about 87% to about 99% 3-tert-butylphenyl chlorothionoformate, and from about 1% to about 13% 4-tert-butylphenyl chlorothionoformate.

4. The process of claim 1 wherein said protecting agent is 1,3-dichloro-1,1,3,3-tetraisopropyldisiloxane.

5. The process of claim 1 wherein said radical reagent is triethylsilyl hydride.

6. The process of claim 1 wherein said radical reagent is a poly(alkyl)hydrosiloxane.

7. The process of claim 6 wherein said radical reagent is poly(methyl)hydrosiloxane.

8. A process for generating a 2'-deoxynucleoside radical comprising the steps of:
   selecting a ribonucleoside;
   treating said ribonucleoside with at least one protecting agent for a time and under conditions effective to form the 3'-O,5'-O-bisprotected ribonucleoside;
   contacting said 3'-O,5'-O-bisprotected ribonucleoside with an isomeric mixture of tert-butylphenyl chlorothionoformates for a time and under conditions effective to form the isomeric 2'-O-tert-butylphenoxythiocarbonyl derivatives of said bisprotected ribonucleoside; and treating said derivatives with a triethylsilyl hydride or poly(alkyl)hydrosiloxane radical reagent and a radical initiator for a time and under conditions effective to form the corresponding 2'-deoxynucleoside radical.

9. The process of claim 8 wherein said isomeric mixture comprises 3-tert-butylphenyl chlorothionoformate and 4-tert-butylphenyl chlorothionoformate.

10. The process of claim 9 wherein said isomeric mixture comprises from about 87% to about 99% 3-tert-butylphenyl chlorothionoformate and from about 1% to about 13% 4-tert-butylphenyl chlorothionoformate.

11. The process of claim 8 wherein said protecting agent is 1,3-dichloro-1,1,3,3-tetraisopropyldisiloxane.

12. The process of claim 8 wherein said radical reagent is a solid supported triethylsilyl hydride.

13. The process of claim 8 wherein said radical reagent is a poly(alkyl)hydrosiloxane.

14. The process of claim 13 wherein said radical reagent is poly(methyl)hydrosiloxane.

15. A process for converting a hydroxyl group to hydrogen comprising the steps of:
   selecting a compound having said hydroxyl group;
   contacting said compound with an isomeric mixture of tert-butylphenyl chlorothionoformates for a time and under conditions effective to form a mixture of isomeric tert-butylphenoxythiocarbonyl derivatives of said compound; and
   treating said derivatives of said compound with a triethylsilyl hydride or poly(alkyl)hydrosiloxane for a time and under conditions effective to convert said hydroxyl group of said compound to hydrogen.

16. The process of claim 15 wherein said isomeric mixture comprises 3-tert-butylphenyl chlorothionoformate and 4-tert-butylphenyl chlorothionoformate.

17. The process of claim 16 wherein said isomeric mixture comprises from about 87% to about 99% 3-tert-butylphenyl chlorothionoformate and from about 1% to about 13% 4-tert-butylphenyl chlorothionoformate.

18. The process of claim 15 wherein said triethylsilyl hydride or poly(alkyl)hydrosiloxane reacts by a radical deoxygenation step.

* * * * *

UNITED STATES PATENT AND TRADEMARK OFFICE
CERTIFICATE OF CORRECTION

PATENT NO.       : 6,822,089 B1
APPLICATION NO.  : 09/537843
DATED            : November 23, 2004
INVENTOR(S)      : Yogesh S. Sanghvi et al.

It is certified that error appears in the above-identified patent and that said Letters Patent is hereby corrected as shown below:

1) Column 20, Claim 15, line 7, please delete "a".

Signed and Sealed this

Twenty-ninth Day of January, 2008

JON W. DUDAS
*Director of the United States Patent and Trademark Office*